(12) United States Patent
Katske et al.

(10) Patent No.: US 7,402,311 B2
(45) Date of Patent: *Jul. 22, 2008

(54) COMPOSITION AND METHOD FOR TREATING NON-BACTERIAL CYSTITIS

(76) Inventors: Floyd A. Katske, 10660 Wilshire Blvd. #1505, Los Angeles, CA (US) 90024; Daniel Shoskes, 3220 Paddock Rd., Weston, FL (US) 33331

( * ) Notice: Subject to any disclaimer, the term of this patent is extended or adjusted under 35 U.S.C. 154(b) by 38 days.

This patent is subject to a terminal disclaimer.

(21) Appl. No.: 10/421,515

(22) Filed: Apr. 22, 2003

(65) Prior Publication Data

US 2004/0213773 A1 Oct. 28, 2004

(51) Int. Cl.
*A61K 38/46* (2006.01)
*A61K 36/45* (2006.01)
*A61K 36/84* (2006.01)
*A61K 36/282* (2006.01)

(52) U.S. Cl. .................. 424/94.65; 424/725; 424/732; 424/733; 424/741

(58) Field of Classification Search .............. 424/94.65, 424/725, 732, 733, 741
See application file for complete search history.

(56) References Cited

FOREIGN PATENT DOCUMENTS

| | | | |
|---|---|---|---|
| CN | 1093591 A | * | 10/1994 |
| CN | 1166982 A | * | 10/1997 |
| RU | 2098155 C1 | * | 12/1997 |
| RU | 2137492 C1 | * | 9/1999 |

OTHER PUBLICATIONS

Shoskes et al., "Quercitin in Men with Category III Chronic Prostatitis: A Preliminary Prospective, Double blind Placebo Controlled Trial", Urology, Dec. 1999, 54(6): 960-3.*
Katske et al., "Treatment of Interstitial Cystitis with a Quercitin Supplement", Tech Urol, Mar. 2001, 7(1):44-6.*
Nanarko, "Infection Control. The Therapeuric uses of Cranberry Juice", Nurs Stand, May 1995; 9(34):33-5.*
http://www.farrlabs.com/products/?keyword=prosta-q.*
http://www.farrlabs.com/products/?keyword=cysta-q.*

* cited by examiner

*Primary Examiner*—Ruth A Davis
(74) *Attorney, Agent, or Firm*—Robert J. Schaap

(57) ABSTRACT

A composition and a method for treatment of urinary tract dysfunction and, particularly, non-bacterial cystitis and, even more particularly, non-bacterial chronic interstitial cystitis. The composition primarily relies upon the use of a bioflavonoid and, particularly, that bioflavonoid known as quercetin. The quercetin is mixed with a proteolytic digestive enzyme protease, such as bromelin and papain, as the primary active ingredients. However, the composition may optionally and beneficially include other cystitis affecting agents, such as cranberry, as well as some other active and non-active ingredients.

22 Claims, 1 Drawing Sheet

COMPOSITION AND METHOD FOR TREATING NON-BACTERIAL CYSTITIS

RELATED APPLICATION

This application is based on and obtains the benefit of my now abandoned U.S. provisional patent application Ser. No. 60/203,486, filed May 9, 2000, for "Composition for Treating Non-Bacterial Cystitis".

BACKGROUND OF THE INVENTION

1. Field of the Invention

The invention primarily relates to a composition and method for the treatment of non-bacterial cystitis and, more particularly, to a composition and method for treating non-bacterial chronic interstitial cystitis syndromes using bioflavonoids in a treatment composition and in a treatment method.

2. Brief Description of the Related Art

Interstitial cystitis represents a non-specific group of urinary tract and, particularly, bladder related problems and is often characterized by pain, which may actually adopt the form of phantom symptomatic pain. Interstitial cystitis is generally a pervasive inflammatory condition of the bladder and can be disabling to a sufferer. The symptoms usually suffered are bladder pain and frequent micturition. (urination). Interstitial cystitis is one of the conditions in which very few of the available therapies are effective.

At present, the cause for this condition is not fully known. As a result, there is frequently no known cure for non-bacterial interstitial cystitis, although there are several therapies of varying effectiveness, and usually of limited effectiveness. These therapies are generally designed to address the issues of pain and discomfort as well as the other symptoms arising from this condition, but are not specific to any effective cure or permanent treatment therefor.

Subjects having chronic interstitial cystitis refractory to conventional therapies often present frustration to a urologist attempting to treat that condition. For patients who do not respond to antibiotic therapy, but have negative fluid cultures, the etiology is unclear. It is recognized that a certain percentage of these patients probably have persistent bacterial infections.

There is still a great deal of controversy concerning the pathophysiology and the treatment which may be appropriate therefor. At present, prolonged antibiotic therapy is common for both the bacterial and the non-bacterial cystitis. However, where microbial therapy has shown itself to be relatively ineffective, other therapies have used alpha-blockers, anti-inflammatory agents and muscles relaxants. Nevertheless, these therapies have only met with variable success. There has been some use of dimethyl sulfoxide in a 50% solution (known as Rimso 50) as an attempt to relieve some of the symptoms of this condition. However, this composition is introduced intervesically, usually by means of a catheter and therefore not an effective home use treatment.

Beyond the therapies which attempt to elevate this condition, anti-pain medication, including various tricylic medications have been employed. Biofeedback for pain control has been also employed. Even surgery has been used as a mode of treatment, but the patient frustration with this type of treatment is relatively high.

The existence of chronic interstitial cystitis syndromes are therefore well known and are common disorders in women, particularly as age progresses. However, very few of the available therapies are effective for treatment of this condition, as aforesaid. There has been some evidence that bioflavonoids in general have improved the symptoms of this disorder in cases where tried. The use of the bioflavonoids has been well tolerated in tests and does provide some slight symptomatic improvement.

There have been some tests with patients using the bioflavonoid quercetin, alone. The symptomatic response of these patients taking quercetin has been significant. However, few patients ever became completely asymptomatic. Severe urinary symptoms in particular were least likely to improve with the quercetin alone. However, pain was controlled.

Today, the available modes of treatment are relatively ineffective or have only limited effectiveness. Thus, there has been a need for some therapy to treat chronic non-bacterial interstitial cystitis.

OBJECTS OF THE INVENTION

It is, therefore, one of the primary objects of the present invention to provide a composition which is effective in treating the symptoms of non-bacterial interstitial cystitis through an anti-inflammatory mechanism.

It is another object of the present invention to provide a composition for treating non-bacterial interstitial cystitis and even chronic non-bacterial interstitial cystitis by use of an enzyme which increases the transmural intestinal absorption of a bioflavonoid for reducing any inflammatory condition.

It is a further object of the present invention to provide a bioflavonoid containing composition which primarily relies upon the use of quercetin, along with a digestive enzyme, for increasing transmural intestinal absorptivity and, hence, the functional bioavailability thereof.

It is an additional object of the present invention to provide a composition of the type stated which relies upon the use of quercetin and a combination of digestive enzymes, including, for example, bromelin and papain.

It is a salient object of the present invention to provide a method of administering a bioflavonoid containing composition to reduce the symptomatic disablement causes by inflammation of the bladder.

With the above and other objects in view, my invention resides in the novel features of form and components forming part of the composition and the method of treatment therefor in the present invention.

BRIEF SUMMARY OF THE INVENTION

The present invention primarily relies upon the use of a bioflavonoid to operate as an anti-inflammatory agent for reducing the symptomatic effects of interstitial cystitis and, particularly, chronic interstitial cystitis. It has been found in connection with the present invention that the most preferred bioflavonoid, which has generally produced excellent results, is that of quercetin. The quercetin appears to operate as an anti-inflammatory agent and reduces inflammation of the bladder lining.

Tests have revealed that the quercetin alone does not have a high bioavailability due to the fact that transmural intestinal absorption is relatively low. It has also been found in connection with the present invention that the use of one or more selected digestive enzymes will substantially increase the bioavailability of the quercetin or similar bioflavonoid and, hence, will improve the treatment of these symptomatic effects. Two of the most effective enzymes thus found to be effective in the present invention include bromelin and papain. Any digestive enzyme having the effects of bromelin and papain is effective, although these two enzymes have been found to be the most effective in accordance with the present invention. The combination of these enzymes, Bromelin and papain, when used together, has also been found to even more substantially increase the bioavailability of the quercetin or other bioflavonoid.

It has also been found that other components in the composition are also effective in the treatment of chronic interstitial cystitis of the non-bacterial type. For example, cranberry has been used to reduce prostatic hyperplasia. The cranberry has been found to be a highly useful herb in the prevention and treatment of urinary tract infections, even though lacking any antiseptic or any anti-bacterial properties, per se. The cranberry actually causes an acidity in the urine and this acid medium actually hinders bacterial development in the urinary tract. The use of cranberries has been found to be effective in preventing urinary tract infection, particularly among women, where other medical treatments were largely ineffective.

It has been found that both bromelin and papain along with quercetin and the cranberry powder are the four most important components in the composition of the present invention, although other components, as hereinafter described, are also effectively used in the treatment composition and in the method of treatment therefor.

In addition to the above, there are other ingredients which are effective in this composition and include, for example, a nervine agent, such as betony, and a kidney stimulant, such as scullcap. Further, a nerve depressant, such as valerian, may also be employed. In addition, a diarrhea treatment agent, such as cohosh black, may be used.

One of the important aspects of the present invention is the fact that the various components identified above are largely herbal blends. Consequently, these ingredients lack the harsh effects which is sometimes found with various pharmaceutical type compositions. Moreover, the composition not only finds an effectiveness greater than any pharmaceutical composition which may be available, but it is also made from natural ingredients.

The composition of this invention may include, for example, titanium dioxide or similar coloring agent as well as one or more other dyes. In this case, the dyes are preferably natural or herbal dyes, to the extent available. Magnesium stearate may similarly be included in the composition as a binding agent. In addition, the composition may be provided with a gelling agent or it may be made available in the form of a tablet.

This invention possesses many other advantages and has other purposes which may be made more clearly apparent from a consideration of the forms in which it may be embodied. These forms are described in detail in the specification and in the accompanying examples therefor. They will now be described in detail for purposes of illustrating the general principles of the invention. However, it is to be understood that the following detailed description and any drawings therefor are not to be taken in a limiting sense.

BRIEF DESCRIPTION OF THE DRAWING

Having thus generally described the invention in general terms, reference will now be made to the accompanying drawing in which.

DETAILED DESCRIPTION OF PREFERRED EMBODIMENTS

Figure 1:
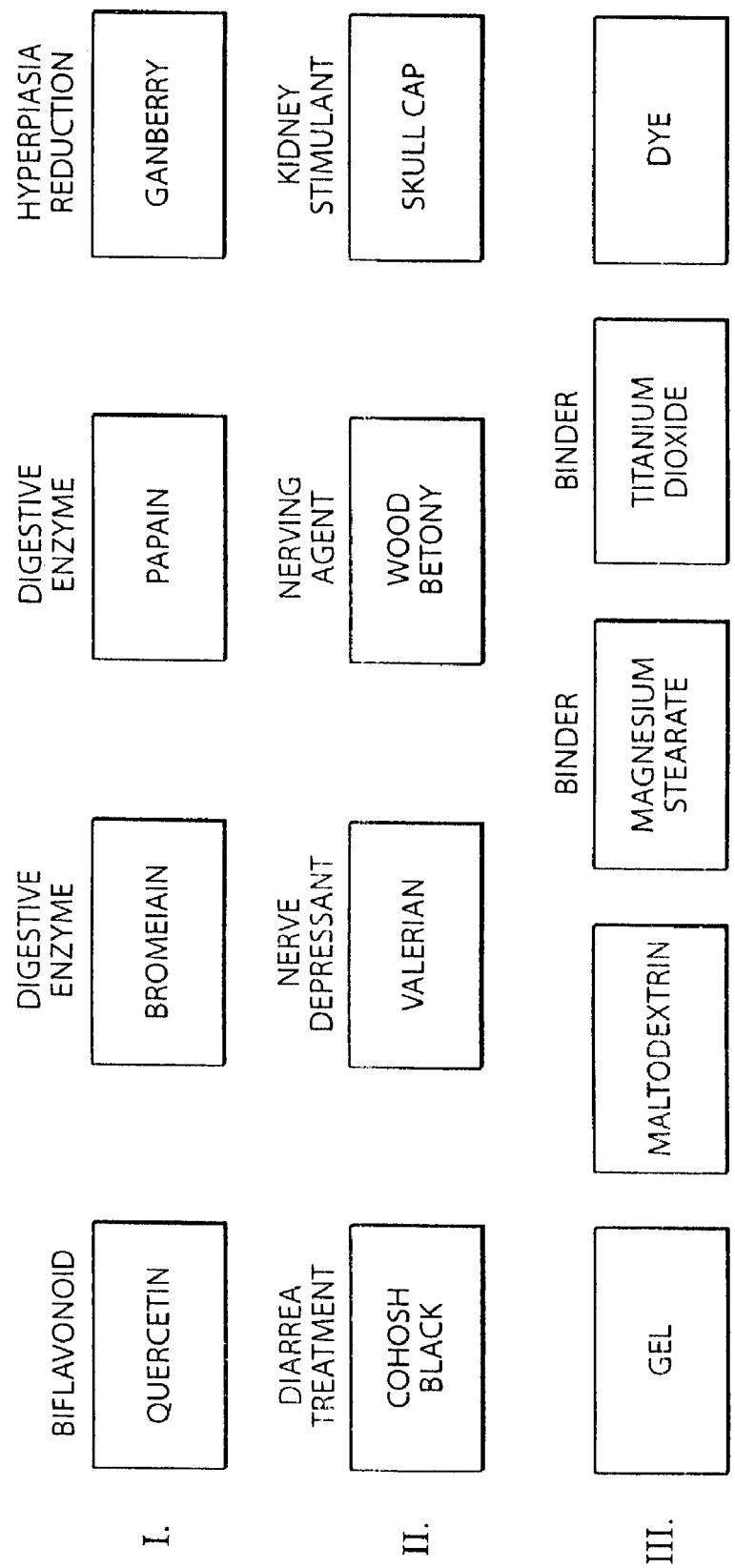
FIG. 1 is a schematic illustration of several levels of components which form part of the composition of the present invention.

The present invention relates to a composition for treating non-bacterial interstitial cystitis and, particularly, non-bacterial chronic interstitial cystitis. The composition largely relies upon the use of a bioflavonoid in combination with one of more digestive enzymes which increase the bioavailability of the bioflavonoid.

There are essentially three levels of components which are used in the composition of the present invention and which are more specifically illustrated in the attached drawing. These three levels are identified as Level I, Level II and Level III, as shown on FIG. 1. These various levels identify those components in order of levels of importance or efficacy in the treatment of interstitial cystitis. It has been found, in accordance with the present invention, that those components identified in Level I are the most contributing ingredients to the efficacy of the composition and with those components identified in Group II as moderately important in contributing to the efficacy of the composition. Finally, the components of Group III are primarily designed to aid in functionality as, for example, imparting color, viscosity and the like.

Level I includes the most important of the component, as aforesaid, such as a bioflavonoid, as well as one or more digestive enzymes. These are the most critical components of the composition, since the digestive enzyme aids in the acceptance of the bioflavonoid by the body, and particularly through transmural intestinal absorption thereby increasing the functional bioavailability of the bioflavonoid. Bioflavonoids are polyphenolic compounds having anti-oxidant properties, both as free radical scavengers and as inhibitors of xanthine oxidase. The anti-inflammatory properties of these bioflavonoids block both chemokines and cytokaines. Furthermore, they possess anti-microbial properties and anti-fungal properties which may well have an impact in a treatment program using the present composition.

One of the most important bioflavonoids which has been found to be efficacious in the present invention is that known as quercetin. The quercetin acts to reduce inflammation, particularly of the bladder liner, and is also used therapeutically to decrease capillary fragility. Quercetin is frequently found in eucalyptus as well as onion plants and other sources. The effects of quercetin as a common natural food ingredient is described by Albert Leung in the Encyclopedia of Common Natural Ingredients Used In Food (1980) published by John Wiley & Sons, New York, page 409 et. seq.

Quercetin can also be derived commercially from blue-green algae and is water soluble and composed of substances which often appear in fruit and vegetables as companions to vitamin C. The quercetin is primarily effective as an anti-oxidant and it is an efficacious oxidation inhibiter. It is known, for example, that linoleic and linolenic acids inhibit immune responses in many cases. Inhibition of the lipid mediator production by quercetin is believed to be, at least in part, responsible for the efficacious results in the treatment of interstitial cystitis.

Although quercetin has been found to be one of the most effective bioflavonoids, others, which have been formally identified as vitamin P, are water soluble and include, for example, citrin, hesperindin, rutin, flavones, flavonals, and curcumin.

The bioavailability of the bioflavonoid is substantially increased with the use of digestive enzymes and, particularly, those enzymes contained in the herbal compounds, bromelin and papain. The exact mechanism for achieving the unique anti-inflammatory mechanism is not fully understood, although it is believed that these enzymes and, particularly, the bromelin and papain, are contributory to the transmural intestinal absorption which thereby gives rise to a substantially increased bioavailability of the flavonoid. Other digestive enzymes can also be used.

The bromelin is a protolytic protease enzyme which is frequently obtained from the juice of a pineapple plant. It has been used as an adjunctive therapy to reduce inflammation and edema and also to accelerate tissue repair. See, for example, M. J. T. Peatson and P. Finnegan, 1968, British Journal of Clinical Practice 22. In this respect, the bromelin actually operates, to some extent, in conjunction with the bioflavonoid to reduce inflammation.

Dietary quercetin has been found to have variable absorption depending upon the source and degree of glycosylation. It is believed that cellular bioavailability may further be compromised by binding of the quercetin to plasma proteins and, particularly, albumin. Thus, it is believed that a combination of the quercetin or other bioflavonoid, along with papain and bromelin or other dietary enzymes, will aid in transporting the bioflavonoid across the intestinal membrane.

As third level components of the composition, a hyperplasia reducing agent or combination thereof is employed. Thus, and for the purposes of this composition, it has been found that cranberry is the most preferred hyperplasia reducing agent. Cranberry is know as a very useful herb for the prevention and treatment of urinary tract infections. Furthermore, inasmuch as bacterial infections frequently accompany interstitial cystitis, a component for treatment of urinary tract infections is also highly desirable. However, cranberry is also know is lack any antiseptic or anti-bacterial properties, per se. It is known that urine of an individual becomes more acid after a large quantity of cranberry is consumed, and this acid medium does hinder bacterial development. However, it is recognized that the effectiveness of cranberry juice and cranberry generally results not necessarily from the acidifying properties, but as a result of the ability to prevent microorganisms from adhering to the epithelial cells of the liner in the urinary tract, such as *escherichia coli*.

It is preferable in accordance with the present invention to use cranberry having a fructose base along with various carbohydrates and fiber and plant acids, such as benzoic acid, citric acid, malic acid and quinic acid.

In the accompanying drawing, cranberry is identified as a Level I component. However, in actuality, cranberry could be identified as a component existing between the Level I components and the Level II components. This is due to the fact that it possibly has a greater effect than do the Level II components, but probably not the same effect as the Level I components. However, it has also been found that the effectiveness of the cranberry is similarly improved when the digestive enzymes are employed in the composition.

It is also possible to use other hyperplasia reducing agents, particularly of the herbal type, such as nettle root, sometimes known as *urica dioica*. Again, the nettle root may be used in addition to or in place of the cranberry or saw palmetto. However, as the second level components, cranberry and saw palmetto are preferred.

In my aforesaid co-pending utility patent application, also entitled "Composition for Treating Non-Bacterial Prostatitis", the bioflavonoid and the digestive enzymes were also employed. In that co-pending application, however, the composition thus developed was effective in the treatment of non-bacterial prostatitis. Nevertheless, it has been found in accordance with the present invention that some of the components used in that other composition for treatment of prostatitis are effective in the treatment of interstitial cystitis in women.

In that composition in the aforesaid utility application and, in particular, in the present application, some of the same Group I level components were also used. This composition also differs from that composition in the aforesaid co-pending utility patent application, in that it uses some different Group II components. The Group II components in the instant invention are designed primarily to have an effect on nerve action of the body. To some extent, it is believed and recognized that nerve action may have some effect on interstitial cystitis. Thus, by addressing this nerve action, it is possible to reduce the symptomatic effects of interstitial cystitis.

The composition of the invention also includes those second level components which are specifically identified in the enclosed FIG. 1 and include a diarrhea treatment agent, such as cohosh black, a nerve depressant, such as valerian, a nervine agent, such as betony, and a kidney stimulant, such as scullcap. As a result, these other Level II components are only briefly described herein. It is important to note, however, that all of the components thus far employed in the composition of the invention and, for that matter, those employed as Level III components, are natural components and, more specifically, all are herbal components.

The scullcap is also an effective tonic for blood impurities. The scullcap is also a nervine agent which provides a neuralgia action. This particular component is available in a variety of forms and includes common scullcap, lesser scullcap, Virginian scullcap, and the like. However, any of these scullcap agents may be used in the invention. Scullcap is known as a strong tonic and a nervine and also has an anti-spasmodic action. It is also a slight astringent. However, the exact mechanism of scullcap in this composition is not known.

Cohosh black has been found to be suitable for a diarrhea treatment. Although it does not appear to function as a diarrhea inhibiting agent in the use of the composition of the invention, its presence has been found at least to be contributory to reduction of some of the symptomatic effects of interstitial cystitis. Consequently, and although its exact mechanism is not known, it is frequently included in the composition of the invention. A nervine agent which is employed is betony and a nerve depressant used is valerian. Here again, these are the most preferred of the nervine agents, and nerve depressants, although other natural nervine agents and nerve depressants could be used in place thereof or, for that matter, in addition thereto. It is possible to use only valerian or for that matter betony, although each are desirable in the composition.

Another one of the Level II components is that of passion flower (sometimes known as "Maypop" or by its biological name of "*Passiflora Incarnata*"). Passion flower can act as a cyanogenic glycoside and has known effects to depress nerve transfer in the spinal cord and in the brain. Moreover, it has somewhat of an effect on depressing the central nervous system. Passion flower is also known to serve as a potential "nerve tonic". Although its effect in the present composition is not fully known, it is believed that it effectively operates as a nerve depressant.

The composition of the invention also includes those Level III components including, for example, magnesium stearate and titanium dioxide. The magnesium stearate and the titanium dioxide both operate as a binder. Titanium dioxide also operates as a coloring agent. Various dextrins can also be used as binding agents to hold the composition in a particulate form, preferably for tableting and the like. Moreover, the composition may include a gelling agent, such as sodium hydroxymethyl cellulose or the like. Natural gelling agents, to the extent available, are preferred. Finally, the composition may include one or more dyes in order to provide a color to the composition. It is preferable to use food dyes where available and, particularly, herbal dyes.

The quercetin or other bioflavonoid is used in predominant amounts in the composition and considering the quercetin and the enzymes alone as the Level I components, the quercetin can range from about 40% to about 97% by weight of the total components in the composition. The digestive enzyme bromelin would also range from about 0.25% to about 20% by weight based on the total weight of the components used in the composition, and the papain would similarly range from about 0.25% to about 20% by weight based on the total weight of the composition. Although smaller amounts of the bioflavonoid can be used, inasmuch as it is one of the most active ingredients in the composition, it should be present in an amount normally of about no less than 30%.

The preferred active components forming part of each dosage of the present composition is set forth in the following Table I. In this Table I, the ideal dosage percentage by weight is set forth along with a general weight percent range which can be used and also a preferred dosage weight percent range. This table does not include the inactive components, such as dyes, etc., since they would be used in amounts necessary to accomplish their intended purpose in the composition. These percent ranges are based on weight, as aforesaid.

TABLE I

Percentage of Components

| | Ideal Dosage Percentage | General Dosage Percentage Range | Preferred Dosage Percentage Range |
|---|---|---|---|
| Quercetin | 83% | 40-97% | 62-94% |
| Cranberry | 6.5% | 0.25-25% | 2.0-18% |
| Bromelin | 4.25% | 0.25-20% | 1.5-12% |
| Papain | 4.25% | 0.25-20% | 1.5-12% |
| Black Cohosh | 0.4% | 0.1-4.0% | 0.1-2.0% |
| Scullcap | 0.4% | 0.1-4.0% | 0.1-2.0% |
| Wood Betony | 0.4% | 0.1-4.0% | 0.1-2.0% |
| Passion Flower | 0.4% | 0.1-4.0% | 0.1-2.0% |
| Valerian | 0.4% | 1.1-4.0% | 0.1-2.0 |

In the composition, the quercetin or other bioflavonoid is preferably used in an amount of about 500 milligrams in a total composition having a total weight of approximately 600 milligrams. However, the quercetin or other bioflavonoid can be present in widely varying amounts, as hereinbefore described in more detail. The amount of the bromelin and the amount of the papain, as well as the other ingredients, therefore could each range as set forth in Table I above.

One preferred composition which has been tested and has effectively reduced symptoms of even chronic non-bacterial interstitial cystitis is that set forth below in the following Table II:

TABLE II

| Components | |
|---|---|
| Quercetin | 500 mg |
| Bromelin | 25 mg |
| Papain | 25 mg |
| Cranberry | 40 mg |
| Black Cohosh | 2 mg |
| Scullcap | 2 mg |
| Wood Betony | 2 mg |

TABLE II-continued

| Components | |
|---|---|
| Valerian Root | 2 mg |
| Gelatin | 120 mg |
| Magnesium Stearate | 19 mg |
| Titanium Dioxide | <1 mg |
| FD & C Red 40 | <1 mg |

These compositions were tableted and taken in an amount of five tablets three times a day. The amount of dosage per day can vary depending on need and severity of condition.

The composition is preferably useful as a dietary supplement. Moreover, due to the fact that the ingredients used in the composition are all natural ingredients, the otherwise deleterious affects of conventional medications used for this purpose are avoided. Although the exact theory for the pathological efficacy of the composition is not known, it is recognized that the quercetin or similar bioflavonoid changes the oxidation potential in the body. The quercetin also has been found to act as a kinase inhibitor and a nitrogen dioxide inhibitor. Hence, the stress level is effectively reduced.

The composition is not offered as a cure fur interstitial cystitis. However, it is an effective symptomatic treatment for interstitial cystitis. The composition is preferably offered as a dietary supplement in capsule form.

EXAMPLES

The invention is further illustrated by, but not limited to, the following examples:

Example I

A composition having the following ingredients and the weight amounts per dosage set forth in the following Table III, is tested with forty subjects:

TABLE III

| | Weight Amount Dosage |
|---|---|
| Quercetin | 500 mg |
| Cranberry Powder | 40 mg |
| Bromelin | 25 mg |
| Papain | 25 mg |
| Black Cohosh | 2 mg |
| Scullcap | 2 mg |
| Wood Betony | 2 mg |
| Valerian Root | 2 mg |
| Passion Flower | 2 mg |
| Gelatin | 120 mg |
| Magnesium Stearate | 19 mg |
| Titanium Dioxide | <1 mg |
| FD & C Red 40 | <1 mg |

Each of the patients consume two to four capsules per day and continue using the capsules until the symptoms abate. It is generally found that, in most cases, the symptoms, such as urinary retention, is reduced, urination commencement is eased, and pain associated with the urinary region has been substantially reduced in about two to five days. However, it was found that in most cases when the use of the composition is stopped, there is a re-initiation of the same symptoms. Thus, it is theorized that the anti-inflammatory mechanism provided by the composition is at least in part responsible for the improved results.

Example II

A double blind study using 30 patients without positive bacterial cultures localized to the prostatic fluid are enrolled in a double blind study. Seventeen of the patients receive a composition comprised of quercetin in amount of 500 milligrams, bromelin in an amount of 10 milligrams, and papain in an amount of 10 milligrams as the active ingredients thereof. After a randomized study is completed, an additional fifteen patients are treated in an open label study with only the bromelin.

The fifteen patients which are randomized to quercetin alone complete the study and two of the fifteen patients randomized to the placebo do not because of worsening symptoms. The mean symptom score improves from 21.0 to 13.1 in the group receiving quercetin, but from 20.2 to 18.8 in the placebo group. This represents an improvement of 35%. In those patients which receive only the quercetin, without the papain and bromelin, with obtainable secretions, the white blood cell count in the decreases from 16.8 to 5.3, versus a decrease from 13.1 to 8.3 in the placebo patients. Thus, patients taking the quercetin along with the digestive enzymes show significantly improved therapy versus those who did not.

This study proves that the patients receiving the quercetin along with at least the papain and the bromelin have superior results compared to patients which received only the quercetin.

Example III

A composition as set forth in the following Table IV is administered to 60 male patients.

TABLE IV

|  | Weight Amount Dosage |
|---|---|
| Quercetin | 500 mg |
| Cranberry Powder | 50 mg |
| Bromelin | 35 mg |
| Papain | 35 mg |
| Black Cohosh | 5 mg |
| Scullcap | 5 mg |
| Wood Betony | 5 mg |
| Valerian Root | 5 mg |
| Passion Flower | 5 mg |
| Other Ingredients: |  |
| Gelatin | 120 mg |
| Magnesium Stearate | 19 mg |
| Titanium Dioxide | <1 mg |
| FD & C Red 40 | <1 mg |

The administration of the tablets again takes place at a rate of two to three tablets per day until such time as the symptoms decrease on a per patient basis, much in the same manner as set forth in Example II. It is found in connection with the composition as set forth in Table IV that there is a greater mean improvement in the female patients who take the composition of Table IV, as opposed to the composition of Table III.

The composition of the invention is preferably useful as a dietary supplement. Moreover, due to the fact that the ingredients used in the composition are all natural ingredients, the otherwise deleterious effects of conventional medications used for this purpose are avoided. Although the exact theory for the pathological efficacy of the composition is not known, it is recognized that the quercetin or similar bioflavonoid changes the oxidation potential in the urinary tract. The quercetin also has been found to act as a kinase inhibitor and a nitrogen dioxide inhibitor. Hence, the stress level is effectively reduced.

The composition is not offered as a cure for either bacterial or non-bacterial chronic interstitial cystitis. However, it is as an effective symptomatic treatment for non-bacterial interstitial cystitis, whether or not chronic. The composition is preferably offered as a dietary supplement in capsule form. Moreover, it should be taken with meals or otherwise as directed by a physician. It should be understood that other components could also be used in the composition of the present invention. Thus, this composition is by no means limited to the specific components or the specific ingredient range as identified.

Thus there has been described and briefly illustrated a unique and novel composition for the treatment of non-bacterial interstitial cystitis and even non-bacterial chronic interstitial cystitis and which is based primarily on the use of natural components. The present invention thereby fulfills all of the objects and advantages which have been sought. It should be understood that many changes, modifications, variations, as well as other uses and applications will become apparent to those skilled in the art after considering this specification. Therefore, any and all such changes, modifications, variations and other uses and applications which do depart from the spirit and scope of the invention are deemed to be covered by the invention.

The invention claimed is:

1. A composition for the symptomatic treatment of non-bacterial interstitial cystitis said composition comprising:
   a) a bioflavonoid comprised of a substantial percentage of quercetin in an amount larger than the amounts of any other ingredients in the composition and exhibits anti-oxidant and anti-inflammatory qualities; and
   b) a digestive enzyme in an amount effective to increase the transmural intestinal absorption and bioavailability of the bioflavonoid, and to facilitate substantial transmural intestinal absorption of the bioflavonoid in a human body wherein absorption of the bioflavonoid is substantially greater than the amount of transmural intestinal absorption and bioavailability which would occur without the enzyme, wherein the enzyme and bioflavonoid composition reduces symptomatic effects of non-bacterial interstitial cystitis with is improved efficacy than the bioflavonoid alone.

2. The composition for the treatment of non-bacterial interstitial cystitis of claim 1 further characterized in that said digestive enzyme is a member selected from the group consisting of bromelain and papain.

3. The composition for the treatment of non-bacterial interstitial cystitis of claim 2 further characterized in that cranberry is present in the composition in an amount sufficient obtain hyperplasia reduction.

4. The composition for the treatment of non-bacterial interstitial cystitis of claim 2 further characterized in that cohosh black and scullcap are present in the composition in an amount sufficient to reduce the symptoms of interstitial cystitis.

5. The composition for the treatment of non-bacterial interstitial cystitis of claim 3 further characterized in that wood betony and valerian root are present in the composition in an amount sufficient to reduce the symptoms of interstitial cystitis.

6. The composition for the treatment of non-bacterial interstitial cystitis of claim 1 further characterized in that said composition is provided in the form of a gel.

7. The composition for the treatment of non-bacterial interstitial cystitis of claim 1 further characterized in that said composition is provided in the form of a tablet.

8. The composition for the treatment of non-bacterial interstitial cystitis of claim 5 further characterized in that said composition comprises as an ingredient which operates as a nervine agent.

9. The composition for the treatment of non-bacterial interstitial cystitis of claim 8 further characterized in that the ingredient which operates as a nervine agent is wood betony.

10. The composition for the treatment of non-bacterial interstitial cystitis of claim 5 further characterized in that said composition comprises as an ingredient which operates as a kidney stimulant.

11. The composition for the treatment of non-bacterial interstitial cystitis of claim 10 further characterized in that the ingredient which operates as a kidney stimulant is scullcap.

12. The composition for the treatment of non-bacterial interstitial cystitis of claim 1 further characterized in that said composition comprises:
   a) cranberry in an amount of about 18% to about 20% based on the total weight of the composition to obtain hyperplasia reduction;
   b) the bioflavonoid being present in an amount of about 40% to about 97% by weight based on the total weight of the composition; and
   c) the digestive enzyme being present in an amount about 0.25% to about 25% by weight based on the total weight of the composition.

13. The composition for the treatment of non-bacterial interstitial cystitis of claim 1 further characterized in that the bioflavonoid is quercetin and the composition comprises two digestive enzymes present amounts effective to increase the transmural intestinal absorption of the bioflavonoid.

14. The composition for the treatment of non-bacterial interstitial cystitis of claim 13 further characterized in that the digestive enzymes are bromelain and papain and each of said enzymes being present in an amount of about 1% to about 15% by weight based on the total weight of the composition.

15. The composition for the treatment of non-bacterial interstitial cystitis of claim 12 further characterized in that a diarrhea treatment agent, a nerve depressant agent, a nervine agent and a kidney stimulant are also present in the composition of the invention.

16. The composition for the treatment of non-bacterial interstitial cystitis of claim 15 further characterized in that diarrhea treatment agent is cohosh black, the nerve depressant agent is valerian, the nervine agent is wood betony, and the kidney stimulant is scullcap.

17. The composition for the treatment of non-bacterial interstitial cystitis of claim 16 further characterized in that each of the wood betony, scullcap, cohosh black and valerian are present in an amount of about 0.1% to about 4% by weight based on the total weight of the composition.

18. A composition for the symptomatic treatment of non-bacterial interstitial cystitis, said composition comprising:
   a) a bioflavonoid comprised of a substantial percentage of quercetin and exhibits anti-oxidant and anti-inflammatory qualities and is present in an amount greater than the amounts of any other ingredients in the composition;
   b) a digestive enzyme comprising bromelain and papain in amounts effective to increase the transmural intestinal absorption and bioavailability of the bioflavonoid so that there is a transmural intestinal absorption of the bioflavonoid in a human body in an amount greater than that which would occur without the enzyme and in an amount to reduce symptomatic effects of non-bacterial interstitial cystitis, wherein the enzyme symptomatic effects of non-bacterial interstitial cystitis with improved efficacy than the bioflavonoid alone the presence of the digestive enzymes.

19. The composition of claim 18 further characterized in that said composition further comprises:
   a) cranberry in an amount effective to reduce hyperplasia.

20. The composition of claim 19 further characterized in that said composition comprises a nervine agent and a kidney stimulant.

21. The composition of claim 20 further characterized in that the nervine agent is wood betony and the kidney stimulant is scullcap.

22. The composition of claim 21 further characterized in that the composition comprises a diarrhea treatment agent primarily comprised of cohosh black, a nerve depressant primarily comprised of valerian, a nervine agent comprised primarily of wood betony, and a kidney stimulant comprised primarily of scullcap.

* * * * *